(12) United States Patent
Higashiyama et al.

(10) Patent No.: US 10,814,084 B2
(45) Date of Patent: Oct. 27, 2020

(54) CUFF-PRESSURE CONTROL DEVICE, CUFF-ATTACHED TRACHEAL TUBE, AND VENTILATOR

(71) Applicant: Murata Manufacturing Co., Ltd., Kyoto (JP)

(72) Inventors: Yuzo Higashiyama, Kyoto (JP); Daisuke Hirayama, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 325 days.

(21) Appl. No.: 15/820,056

(22) Filed: Nov. 21, 2017

(65) Prior Publication Data
US 2018/0093057 A1 Apr. 5, 2018

Related U.S. Application Data

(63) Continuation of application No. PCT/JP2016/064424, filed on May 16, 2016.

(30) Foreign Application Priority Data

May 27, 2015 (JP) .................................. 2015-107364

(51) Int. Cl.
*A61M 16/04* (2006.01)
*A61M 16/00* (2006.01)

(52) U.S. Cl.
CPC ........ *A61M 16/044* (2013.01); *A61M 16/024* (2017.08); *A61M 16/04* (2013.01);
(Continued)

(58) Field of Classification Search
CPC ........ A61M 25/1018; A61M 25/10184; A61M 25/10187; A61M 16/04; A61M 16/0402;
(Continued)

(56) References Cited

U.S. PATENT DOCUMENTS 4,178,940 A * 12/1979 Au ........................ A61M 16/04
128/207.15
5,235,973 A * 8/1993 Levinson ............ A61M 16/044
128/205.23
(Continued)

FOREIGN PATENT DOCUMENTS

JP 2001-526943 A 12/2001
JP 2011-194222 A 10/2011
(Continued)

OTHER PUBLICATIONS

International Search Report for PCT/JP2016/064424 dated Jul. 12, 2016.
Written Opinion for PCT/JP2016/064424 dated Jul. 12, 2016.

*Primary Examiner* — Timothy A Stanis
*Assistant Examiner* — Thao Tran
(74) *Attorney, Agent, or Firm* — Pearne & Gordon LLP (57) ABSTRACT

A cuff-pressure control device includes a pump, an inner pipe connected to the pump, a pressure sensor that measures an internal pressure of the inner pipe, and a control unit that controls a cuff pressure. A cuff is separable from the cuff-pressure control device, and, in a separation state, a first space in communication with the cuff is kept airtight such that the cuff pressure is maintained. The control unit adjusts a pressure in the cuff-pressure control device to a pressure of the first space before the cuff is connected to the cuff-pressure control device in a connection state in which the cuff in the separation state is connected to the cuff-pressure control device and the cuff and the inner pipe are in communication with each other.

17 Claims, 6 Drawing Sheets

(52) U.S. Cl.
CPC ............... *A61M 2016/0027* (2013.01); *A61M 2205/0294* (2013.01); *A61M 2205/15* (2013.01)

(58) Field of Classification Search
CPC .......... A61M 16/0409; A61M 16/0434; A61M 16/045; A61M 16/0452; A61M 16/044; A61M 16/024; A61M 2205/15; A61B 17/1355; A61B 5/022; A61B 1/00082; A61F 2/958; A61J 15/0042; B60C 23/001; B60S 5/046
See application file for complete search history.

(56) References Cited

U.S. PATENT DOCUMENTS

| | | | | |
|---|---|---|---|---|
| 5,891,277 | A  * | 4/1999 | Bachhuber | B60S 5/046 |
| | | | | 141/197 |
| 6,647,984 | B1 * | 11/2003 | O'Dea | A61M 16/044 |
| | | | | 128/207.15 |
| 7,273,053 | B2 | 9/2007 | Zocca et al. | |
| 2003/0101998 | A1 | 6/2003 | Zocca | |
| 2010/0252048 | A1 * | 10/2010 | Young | A61M 16/044 |
| | | | | 128/207.15 |
| 2012/0283984 | A1 * | 11/2012 | Peng | B60S 5/046 |
| | | | | 702/138 |
| 2013/0178752 | A1 * | 7/2013 | Kodama | A61B 5/0235 |
| | | | | 600/498 |
| 2014/0261442 | A1 * | 9/2014 | Graboi | A61M 16/044 |
| | | | | 128/207.15 |
| 2015/0202931 | A1 * | 7/2015 | Honig | B60C 23/001 |
| | | | | 152/416 |
| 2016/0038699 | A1 | 2/2016 | Higashiyama | |

FOREIGN PATENT DOCUMENTS

| | | |
|---|---|---|
| JP | 2013-056211 A | 3/2013 |
| WO | 2014/174957 A1 | 10/2014 |

* cited by examiner

CUFF-PRESSURE CONTROL DEVICE, CUFF-ATTACHED TRACHEAL TUBE, AND VENTILATOR

This is a continuation of International Application No. PCT/JP2016/064424 filed on May 16, 2016 which claims priority from Japanese Patent Application No. 2015-107364 filed on May 27, 2015. The contents of these applications are incorporated herein by reference in their entireties.

FIELD OF THE DISCLOSURE

The present disclosure relates to a cuff-pressure control device, a cuff-attached tracheal tube, and a ventilator. More specifically, the present disclosure relates to a cuff-pressure control device that is used to appropriately maintain the internal pressure of a cuff, and a cuff-attached tracheal tube and a ventilator that include the cuff-pressure control device.

DESCRIPTION OF THE RELATED ART

In the medical field related to, for example, a ventilator, it has been known that, during tracheal intubation, an operator such as a doctor inserts a tracheal tube into the trachea of the subject (mainly, the human body) from the oral cavity or the nasal cavity to ensure the respiratory tract, and oxygen is fed to the lungs via the tracheal tube. In the case where a space is created between the tracheal tube and the inner wall of the trachea during tracheal intubation, there is a risk that secretions such as saliva or gastric juice flow into the trachea and that the subject develops ventilator-associated pneumonia. A cuff is disposed around the outer wall of the tracheal tube to prevent the secretions from flowing therein.

The cuff is a bag-like member that expands when a gas is supplied to the inside thereof. The space between the tracheal tube and the inner wall of the trachea can be blocked in a manner in which a gas is supplied to the inside of the cuff from an air pump via a connection path to cause the cuff to expand. Thus, the secretions can be prevented from flowing into the trachea.

However, when cuff pressure increases to more than a predetermined range, the expanding cuff presses the blood vessels of the mucosal tissue of the trachea. The pressure to the blood vessels brings about an ischemia state. Consequently, there is a risk of, for example, necrosis and bleeding. When the cuff pressure is less than the predetermined range, the expansion of the cuff is not sufficient, a space is created between the outer circumferential surface of the cuff and the inner wall of the trachea, and secretions such as saliva or gastric juice flow into the trachea in some cases.

For this reason, it is necessary to monitor the cuff pressure to control the cuff pressure such that the cuff pressure is within the predetermined range. For example, Patent Document 1 (Japanese Unexamined Patent Application Publication No. 2011-194222) discloses a cuff-pressure control device for controlling such that the cuff pressure is within the predetermined range.

It is necessary to know the cuff pressure in order to control the cuff pressure. Accordingly, the cuff-pressure control device typically includes a pressure sensor for measuring the cuff pressure. However, in the case of an existing cuff-pressure control device as disclosed in Patent Document 1, it is difficult to directly measure the pressure of the cuff located in the trachea. Accordingly, the cuff pressure is indirectly measured in a manner in which the internal pressure of a pipe (inner pipe) in communication with the cuff in the device is measured with the pressure sensor.

Patent Document 1: Japanese Unexamined Patent Application Publication No. 2011-194222

BRIEF SUMMARY OF THE DISCLOSURE

However, since the actual cuff pressure (real cuff pressure) is not directly measured, there is a problem in that the cuff pressure cannot be accurately measured in some cases.

Ideally, the cuff-pressure control device is connected to the cuff and is continuously used in this state to always maintain a constant cuff pressure. In reality, it is assumed that the cuff-pressure control device is used such that after the cuff is expanded so as to have an appropriate value, the cuff-pressure control device is detached from the cuff (spot use). In the case of such spot use, the cuff-pressure control device is connected to the cuff every predetermined time, the cuff pressure is checked to adjust the cuff pressure to an appropriate pressure, and subsequently, the cuff-pressure control device is detached.

The cuff pressure is checked not only to check whether the cuff pressure is the appropriate value but also to check whether air leak from the cuff occurs. In the case where the cuff pressure is lower than the appropriate pressure, the occurrence of the air leak is confirmed. In the case where the air leak occurs, a treatment such as replacement of the tracheal tube is necessary.

However, when the cuff-pressure control device is connected to the cuff, the volume of a space in communication with the cuff increases by a volume corresponding to the internal volume of, for example, the inner pipe and a connection tube of the cuff-pressure control device, and accordingly, the cuff pressure is lower than that before the connection. For this reason, the cuff pressure before the connection, which is originally expected to be measured, cannot be measured, and there is a problem in that it is difficult to accurately decide whether the air leak occurs.

When the pump does not operate, the internal pressure of the inner pipe is equal to the cuff pressure, and accordingly, the cuff pressure can be measured in a manner in which the internal pressure of the inner pipe is measured with the pressure sensor. However, while the pump operates to pressurize the cuff, air flows through a narrow passage (for example, an inflation tube) connected to the cuff, and accordingly, the internal pressure of the inner pipe is higher by a pressure loss of the passage than the actual cuff pressure. For this reason, there is a problem in that the cuff pressure cannot be accurately measured by merely measuring the internal pressure of the inner pipe with the pressure sensor. In the case where the cuff pressure is controlled on the basis of the measured value of the internal pressure of the inner pipe, the pump is stopped before the actual cuff pressure reaches the predetermined value, and there is a risk that the pressure applied to the cuff is not sufficient.

The present disclosure is accomplished in view of the above problems, and it is an object of the present disclosure to provide a cuff-pressure control device, a cuff-attached tracheal tube, and a ventilator that enable the cuff pressure to be accurately measured.

[1] A cuff-pressure control device used to appropriately maintain a cuff pressure that is a pressure of an inside of a cuff includes a pump that supplies a gas to the inside of the cuff, an inner pipe connected to the pump, a pressure sensor that measures a pressure of an inside of the inner pipe, and a control unit that causes the pump to operate and thereby controls the cuff pressure. The cuff is separable from the cuff-pressure control device, and, in a separation state in which the cuff is separated from the cuff-pressure control device, a first space in communication with the cuff is kept airtight such that the cuff pressure is maintained at a predetermined pressure. The control unit adjusts a pressure in the cuff-pressure control device to a pressure of the first space before the cuff is connected to the cuff-pressure control device in a connection state in which the cuff in the separation state is connected to the cuff-pressure control device and the cuff and the inner pipe are in communication with each other.

[2] In the cuff-pressure control device described in [1], the control unit causes the pressure sensor to measure a pressure P2 of a second space in communication with the cuff and the inner pipe without operating the pump. The control unit calculates the cuff pressure that is equal to a pressure P1 of the first space in the separation state right before the connection state by using the pressure P2 of the second space and the following expression (1).

$$P1=P2 \cdot V2/V1 \qquad (1)$$

(where V1 is a volume of the first space, and V2 is a volume of the second space)

[3] In the cuff-pressure control device described in [1] or [2], the control unit (i) causes the pump to operate for a predetermined time to pressurize a third space in communication with the inner pipe in the separation state, causes the pressure sensor to measure a pressure P30 of the third space before pressurization and a pressure P31 of the third space after the pressurization, and calculates a ratio α of P31 to P30. The control unit (ii) causes the pump to operate for the predetermined time to pressurize the second space in the connection state and in a state where the cuff expands and an increase in a volume of the cuff when the first space is pressurized is ignorable, causes the pressure sensor to measure a pressure P20 of the second space before pressurization and a pressure P21 of the second space after the pressurization, and calculates a ratio β of P21 to P20. The control unit (iii) calculates V2/V1 by using α, β, and the following expression (2).

$$V2/V1=(\beta-1)/(\alpha-\beta)+1 \qquad (2)$$

[4] In the cuff-pressure control device described in any one of [1] to [3], the control unit detects an air-leak state in which the first space is not kept airtight in the separation state and notifies the air-leak state in a case where P1 is lower than the predetermined pressure.

[5] A cuff-pressure control device used to appropriately maintain a cuff pressure that is a pressure of an inside of a cuff includes a pump that supplies a gas to the inside of the cuff, an inner pipe connected to the pump, a pressure sensor that measures a pressure of an inside of the inner pipe, and a control unit that causes the pump to operate and thereby controls the cuff pressure. The control unit causes the pressure sensor to continuously measure the pressure of the inside of the inner pipe while the gas is supplied to the inside of the cuff in a deflated state with the pump. The control unit acquires a first pressure that is the pressure of the inside of the inner pipe that is measured with the pressure sensor and suspends the operation of the pump at a first juncture after the supply of the gas to the inside of the cuff is started and the pressure of the inside of the inner pipe reaches equilibrium for the first time. The control unit acquires a second pressure that is the pressure of the inside of the inner pipe that is measured with the pressure sensor at a second juncture after the operation of the pump is stopped and the pressure of the inside of the inner pipe reaches equilibrium. The control unit causes the pump to operate after the second juncture and then calculates a correction value of the cuff pressure in a manner in which an absolute value of a difference between the first pressure and the second pressure is subtracted from the pressure of the inside of the inner pipe that is measured with the pressure sensor, and causes the pump to operate in accordance with the correction value to control the cuff pressure.

[6] In the cuff-pressure control device described in any one of [1] to [5], the pump is a piezoelectric pump.

[7] A cuff-attached tracheal tube includes the cuff-pressure control device described in any one of [1] to [6], a tracheal tube having a main passage through which a gas is supplied to an inside of a trachea, and the cuff.

[8] A ventilator includes the cuff-attached tracheal tube described in [7].

The present disclosure can provide a cuff-pressure control device, a cuff-attached tracheal tube, and a ventilator that enable the cuff pressure to be accurately measured.

DETAILED DESCRIPTION OF THE DISCLOSURE

Embodiments of the present disclosure will hereinafter be described with reference to the drawings. In the drawings, like reference signs designate like or corresponding components. The relationship between dimensions such as the length, width, thickness, and depth is appropriately changed for clarification and simplification of the drawings and does not represent the relationship between the actual dimensions.

The embodiments are described by way of example. It goes without saying that features described according to the embodiments can be partially replaced or combined. In embodiments beyond a second embodiment, descriptions of common matters to those in a first embodiment are omitted, and only different matters will be described. In particular, the same effects achieved by the same structure are not described in all of the embodiments.

First Embodiment

Before the features of a cuff-pressure control device according to the present embodiment are described, typical structures and functions of the cuff-pressure control device and a cuff-attached tracheal tube according to the present embodiment will be described with reference to the drawings.

Figure 1:
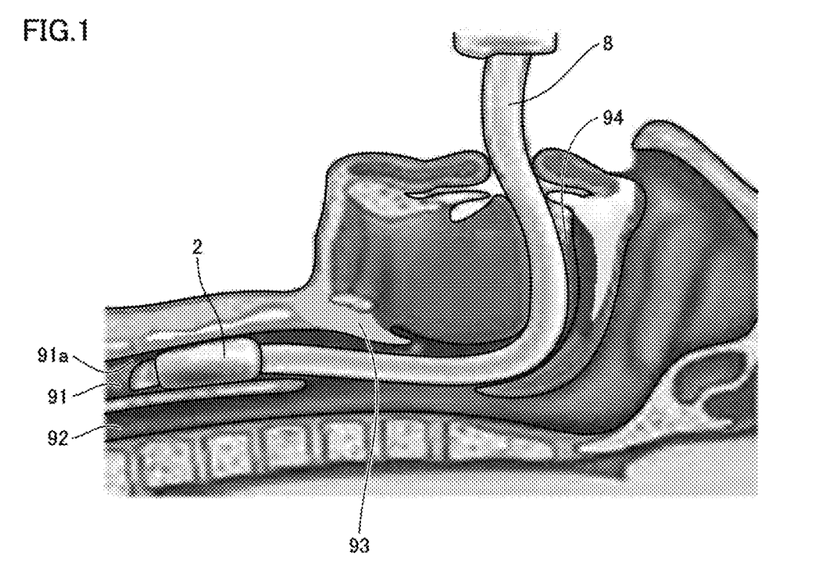
FIG. 1 schematically illustrates a state where a tracheal tube is inserted in the trachea from the oral cavity.

FIG. 1 schematically illustrates a state where a tracheal tube 8 is inserted in the trachea from the oral cavity. In the case where the respiratory tract is ensured by tracheal intubation during use of a ventilator, the tracheal tube (intratracheal tube or intubation tube) 8 is inserted into the trachea 91 from the oral cavity 94 of a subject. At this time, the epiglottis 93 is always opened. Accordingly, there is a risk that secretions such as saliva flow into the trachea 91 from a space between the inserted tracheal tube 8 and an inner wall 91a of the trachea 91, and that the subject develops ventilator-associated pneumonia (VAP).

A cuff 2 is disposed at a predetermined position around the outer circumference of the tracheal tube 8 to prevent such secretions from flowing therein. The cuff 2 can be expanded by being supplied with air from the outside of the body via an air supply tube (not illustrated) described later. When the cuff 2 is expanded, the outer circumferential surface of the cuff 2 comes into contact with the inner wall 91a of the trachea 91, and the space between the tracheal tube 8 and the inner wall 91a of the trachea 91 is blocked. The use of such a cuff-attached tracheal tube enables the respiratory tract to be ensured by using the tracheal tube 8 and prevents, for example, secretions from flowing into the trachea 91 by using the cuff 2.

In this case, the internal pressure (cuff pressure) of the cuff 2 needs to be appropriately maintained. A low cuff pressure causes the space between the tracheal tube 8 and the inner wall 91a of the trachea 91. An excessive cuff pressure impedes the blood flow of a respiratory tract mucosa and damage the mucosa. For example, in the case where the cuff has a low pressure and a large capacity, an appropriate cuff pressure is no less than 20 cmH$_2$O and no more than 30 cmH$_2$O.

According to the present disclosure, the "cuff" is a bag-like member that enables the inside to have a predetermined pressure in a manner in which the inside is filled with a predetermined amount of gas. The cuff is not particularly limited provided that the cuff can adjust the internal pressure, and examples thereof include a balloon of a balloon catheter in addition to a member that is generally called a cuff.

Figure 2:
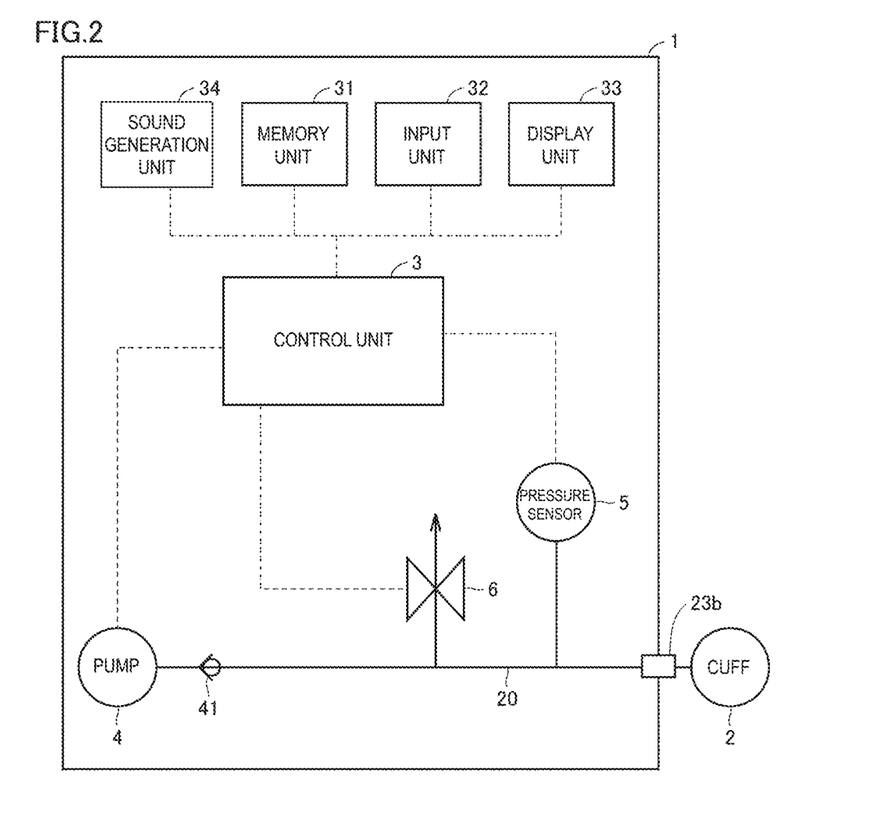
FIG. 2 is a schematic block diagram illustrating the structure of a cuff-pressure control device according to a first embodiment.

FIG. 2 is a schematic block diagram illustrating the structure of a cuff-pressure control device 1 according to the present embodiment. Referring to FIG. 2, the cuff-pressure control device 1 according to the present embodiment is used to appropriately maintain the cuff pressure (pressure of the inside of the cuff 2) and fundamentally includes a pump 4 that supplies a gas such as air to the inside of the cuff 2, an inner pipe 20 connected to the pump 4, a pressure sensor 5 that measures the pressure (gage pressure) of the inside of the inner pipe 20, and a control unit 3 that causes the pump 4 to operate and thereby controls the cuff pressure. The gage pressure is a difference between absolute pressure and atmospheric pressure and is relative pressure when the atmospheric pressure is zero.

A specific example of the pressure sensor 5 is, but not limited to, a piezoresistive pressure sensor, which is MEMS (Micro Electro Mechanical Systems) typically used. This pressure sensor typically performs zero adjustment (zero offset) in which the value of the atmospheric pressure is set to zero.

A piezoelectric pump is preferably used as the pump 4 because the piezoelectric pump facilitates fine adjustment of the amount of air to be supplied to the inside of the cuff 2 and enables the cuff pressure to be controlled with high precision, but the pump is not particularly limited thereto. The inner pipe 20 connected to the pump 4 may include a check valve 41 for maintaining the cuff pressure when the pump 4 is not operated. However, in the case where the pump 4 itself has a checking function, the check valve 41 is not necessary.

The cuff-pressure control device 1 also includes an exhaust valve 6. An example of the exhaust valve 6 may be an electromagnetic valve (solenoid valve), but the exhaust valve is not limited thereto. The exhaust valve 6 is not essential for the cuff-pressure control device according to the present embodiment.

The pump 4 of the cuff-pressure control device 1 is connected to the cuff 2 in a state where a connection path including the inner pipe 20 is interposed therebetween. The gage pressure (cuff pressure) of the inside of the cuff 2 is controlled by the cuff-pressure control device 1 such that the gage pressure is the appropriate value described above.

The control unit 3 compares a predetermined pressure (the predetermined pressure can be changed by an input unit 32) registered in a memory unit 31 and the cuff pressure measured with the pressure sensor 5, and controls at least the operation of the pump 4 in accordance with a difference between these pressures. The pressure sensor 5 directly measures the gage pressure of the inside of the inner pipe 20 and, consequently, indirectly measures the gage pressure (cuff pressure) of the inside of the cuff 2. The control unit 3 is formed of, for example, a memory control unit (MCU).

Specifically, since the cuff pressure is lower than the predetermined pressure at the beginning, the pump 4 is operated, and air is supplied to the inside of the cuff 2 to increase the cuff pressure. At this time, the exhaust valve 6 is in a N.C. (normally closed) state and closes. The cuff pressure is continuously measured while the pump 4 is operated, and the pump 4 is stopped when the cuff pressure increases and reaches the predetermined pressure.

When the diameter of the trachea changes due to, for example, a change in the posture of a patient after the pump 4 is stopped, the cuff pressure becomes larger than the predetermined pressure in some cases. In the case where the cuff pressure is thus larger than the predetermined pressure, the cuff-pressure control device 1 connected to the cuff 2 enables the cuff pressure to be decreased in a manner in which the exhaust valve 6 is opened to discharge air from the inside of the cuff 2. When the cuff pressure is decreased to the predetermined pressure again, the exhaust valve 6 is closed. Thus, the control unit 3 may control the exhaust valve 6 such that the cuff pressure becomes the predetermined pressure.

A display unit 33 displays the measured value of the cuff pressure (correction value), the predetermined pressure of the cuff pressure, and a warning when an abnormality occurs. A sound generation unit 34 provides a warning when an abnormality occurs.

Figure 3A:
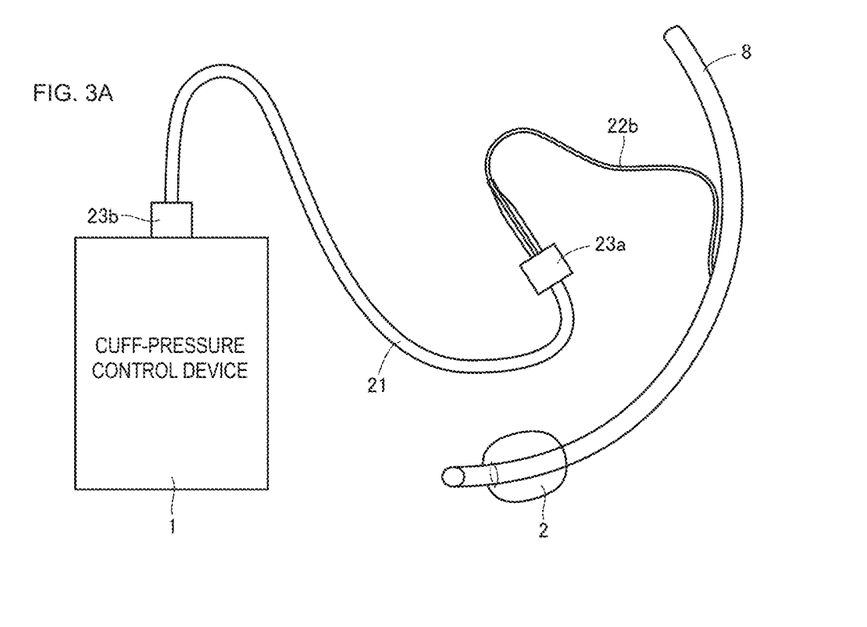
FIG. 3A is a schematic view of a cuff-attached tracheal tube including the cuff-pressure control device according to the first embodiment.
Figure 3B:
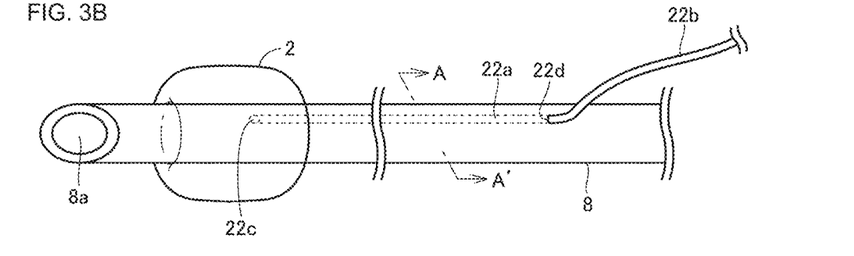
FIG. 3B is an enlarged schematic view of an end portion of the cuff-attached tracheal tube illustrated in FIG. 3A.
Figure 3C:
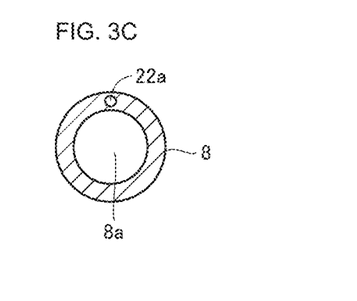
FIG. 3C is a schematic sectional view of FIG. 3B taken along a section A-A'.

FIG. 3A is a schematic view of the cuff-attached tracheal tube including the cuff-pressure control device according to the present embodiment. FIG. 3B is an enlarged schematic view of an end portion of the cuff-attached tracheal tube illustrated in FIG. 3A. FIG. 3C is a schematic sectional view of FIG. 3B taken along a section A-A'.

In the cuff-attached tracheal tube according to the present embodiment, an inflation passage in communication with the inside of the cuff 2 disposed on the tracheal tube 8 is connected to the inner pipe 20 of the cuff-pressure control device 1 with a connection tube 21 interposed therebetween. A luer connector 23a connects an end of the connection tube 21 to an inflation tube 22b. A luer connector 23b connects the other end of the connection tube 21 to the inner pipe 20 (FIG. 2) in the cuff-pressure control device 1.

A first space is formed of the inside of the cuff 2 and the inflation passage (passage 22a and the inside of the inflation tube 22b). A third space is formed of the inside of the inner pipe 20 and the inside of the connection tube 21. A second space is a space formed of the first space and the third space that are coupled with each other.

Thus, the connection path connecting the pump 4 and the cuff 2 to each other is formed of the inner pipe 20, the connection tube 21, and the inflation passage (passage 22a and the inflation tube 22b). The cuff 2, the connection tube 21, the inflation tube 22b, and the tracheal tube 8 are formed of, for example, polyvinyl chloride or olefin-based elastomer.

The inflation passage is formed of the passage 22a (FIG. 3B and FIG. 3C) and the inflation tube 22b (FIG. 3A). As illustrated in FIG. 3C, the passage 22a is formed parallel with a main passage 8a inside a wall portion defining the main passage 8a of the tracheal tube 8 and is not in communication with the main passage 8a of the tracheal tube 8. The passage 22a is in communication with the inside of the cuff 2 via an opening 22c that opens to an outer side portion of the tracheal tube 8. The passage 22a is also in communication with the inside of the inflation tube 22b via an opening 22d that opens to another outer side portion of the tracheal tube 8. The inner diameter of the inflation passage (inflation tube 22b and the passage 22a) is typically smaller than the inner diameter of the connection tube 21.

The inflation passage in communication with the inside of the cuff 2 disposed on the tracheal tube 8 and the inner pipe 20 of the cuff-pressure control device 1 may be directly connected to each other in a state where the connection tube 21 is not interposed therebetween.

The features of the cuff-pressure control device according to the present embodiment and other components will now be described. According to the present embodiment, it is assumed that the cuff-pressure control device 1 is used such that after the cuff 2 is expanded so as to have a predetermined appropriate value (predetermined pressure), the cuff-pressure control device 1 is detached from the cuff 2 (spot use). That is, the cuff-pressure control device 1 is connected to the cuff 2 every predetermined time, the cuff pressure is checked to adjust the cuff pressure to an appropriate pressure, and subsequently, the cuff-pressure control device 1 is detached. When the cuff pressure is checked, whether the cuff pressure is the appropriate value is checked, and whether air leak from the cuff 2 does not occur is checked.

The cuff-pressure control device 1 according to the present embodiment can be separated from the cuff 2 in a manner in which the pump 4 is operated to feed a gas to the inside of the cuff 2, and the connection tube 21 is extracted from the luer connector 23a disposed at the end portion of the inflation tube 22b opposite the cuff 2 after the cuff pressure reaches the predetermined pressure.

The luer connector 23a includes a check valve, and air on the side of the cuff 2 does not escape even when the connection tube 21 is extracted from the luer connector 23a. Thus, the cuff-pressure control device 1 (cuff-pressure control device 1 and the connection tube 21) and the cuff 2 (cuff 2, the inflation passage, and the tracheal tube 8) can be separated from each other while the cuff pressure is maintained. Subsequently, the connection tube 21 may be extracted from the luer connector 23b of the cuff-pressure control device 1.

That is, according to the present embodiment, the cuff 2 can be separated from the cuff-pressure control device 1. In a state where the cuff 2 is separated from the cuff-pressure control device 1 (in the description, this state is also referred to simply as a "separation state"), the first space (space formed of the inside of the cuff 2 and the inflation passage) in communication with the cuff 2 is kept airtight, and the cuff pressure is thereby maintained at the predetermined pressure. The predetermined pressure is selected from the above appropriate values of the cuff pressure in accordance with, for example, the size of the cuff 2.

In a state where the cuff 2 in the separation state is connected to the cuff-pressure control device 1, and the cuff 2 and the inner pipe 20 are in communication with each other (in the description, this state is also referred to simply as a "connection state"), the control unit 3 adjusts the pressure in the cuff-pressure control device to the pressure of the first space before the cuff is connected to the cuff-pressure control device.

Specifically, in the above "connection state", the control unit 3 causes the pressure sensor 5 to measure the gage pressure (internal pressure of the inner pipe 20) of the inside of the inner pipe 20 without operating the pump 4. The internal pressure of the inner pipe 20 is equal to the gage pressure of the second space (space in communication with the cuff 2 and the inner pipe 20), and the gage pressure of the second space can be measured with the pressure sensor 5.

Subsequently, the control unit 3 calculates the cuff pressure that is equal to a gage pressure P1 of the first space in the separation state (before the cuff-pressure control device 1 is connected to the cuff 2) right before the connection state by using a gage pressure P2 of the second space and the following expression (1).

$$P1 = P2 \cdot V2/V1 \qquad (1)$$

In the above expression (1), V1 is the volume of the first space, and V2 is the volume of the second space.

Figure 4:
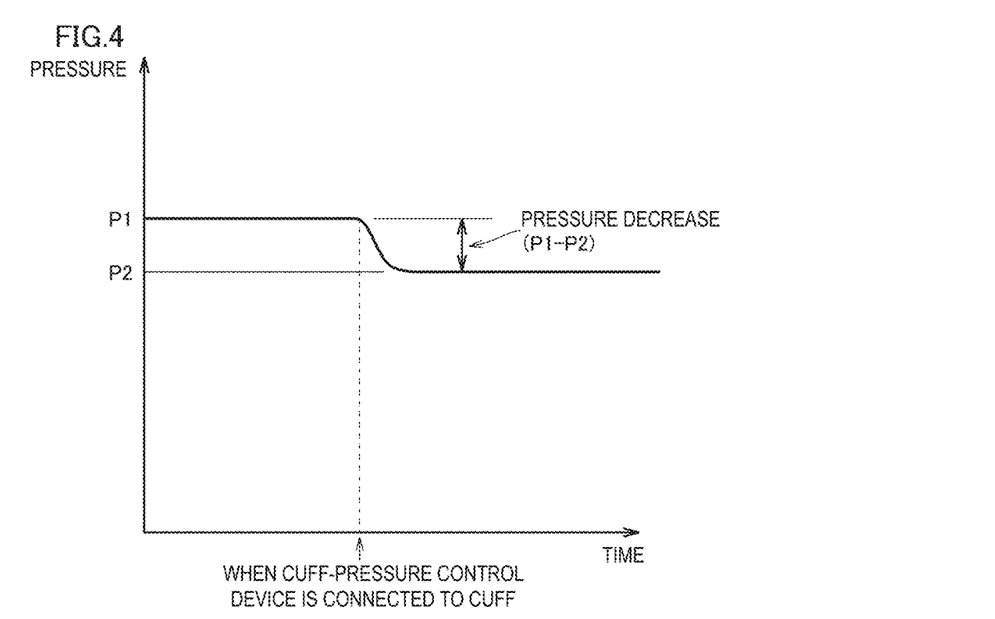
FIG. 4 schematically illustrates a graph of variation in pressure in an inner pipe before and after the cuff-pressure control device is connected to a cuff.

Thus, when the cuff-pressure control device 1 is connected to the cuff 2 that is expanded in advance to check the cuff pressure, pressure decrease (see FIG. 4) caused by the connection of the cuff-pressure control device 1 can be corrected. Accordingly, the right cuff pressure can be monitored, and the occurrence of air leak from the cuff 2 can be easily decided in the case where the correction value of the cuff pressure is lower than the predetermined pressure. Consequently, the pressure decrease due to, for example, air leak can be accurately detected, and safety during a treatment with the cuff can be improved.

According to the present embodiment, the control unit 3 calculates a ratio (V2/V1) of the volume V2 of the second space to the volume V1 of the first space in advance by using a method described in (i) to (iii) below.

(i) In the separation state in which the cuff 2 is separated, the pump 4 of the cuff-pressure control device 1 (in a state where the cuff 2 is not connected thereto) is operated for a predetermined time T to pressurize the third space in communication with the inner pipe 20, a gage pressure P30 of the third space before pressurization and a gage pressure P31 of the third space after the pressurization are measured with the pressure sensor 5 (in a manner in which the internal pressure of the inner pipe 20 is measured with the pressure sensor 5), and a ratio α (P31/P30) of P31 to P30 is calculated.

At this time, an air outlet of the connection tube 21 connected to the cuff-pressure control device 1 is closed to pressurize the third space. It is only necessary to calculate the ratio α once, provided that the dimensions of the connection tube 21 and other components are not changed.

(ii) Subsequently, the pump 4 is operated for the predetermined time T (the same time as the above (i)) to pressurize the second space in the connection state in which the cuff 2 and the cuff-pressure control device 1 are connected to each other and in a state where the cuff 2 expands and an increase in the volume of the cuff 2 when the first space is pressurized is ignorable. A gage pressure P20 of the second space before pressurization and a gage pressure P21 of the second space after the pressurization are measured with the pressure sensor 5 (in a manner in which the internal pressure of the inner pipe 20 is measured with the pressure sensor 5). A ratio β (P21/P20) of P21 to P20 is calculated.

For example, to check the pressure of the cuff 2 that is expanded in advance, the cuff-pressure control device 1 that is switched off is connected to the cuff 2, which brings about the connection state. Subsequently, the cuff-pressure control device 1 is switched on, and the pump 4 is operated for the predetermined time (the same time as T in the above (i)) to pressurize the second space. At this time, the gage pressure P20 of the second space and the gage pressure P21 of the second space after the pressurization are measured with the pressure sensor 5, and β=P21/P20 is calculated with the control unit 3.

(iii) Subsequently, V2/V1 is calculated by using α, β, and the following expression (2):

$$V2/V1 = (\beta-1)/(\alpha-\beta) + 1. \quad (2)$$

The basis of the above expression (2) will now be described.

The calculated α in the above (i) is expressed as:

$$\alpha = P11/P10 = (V3+Q)/V3,$$

where Q is the volume of air supplied by the pump 4, and V3 is the volume of the third space. Accordingly, V3 is expressed as:

$$V3 = Q/(\alpha-1). \quad (A)$$

Since the volume V2 of the second space is equal to the sum (V1+V3) of the volume V1 of the first space and the volume V3 of the third space, the calculated β in the above (ii) is expressed as:

$$\beta = P21/P20 = (V2+Q)/V2 = (V1+V3+Q)/(V1+V3).$$

Substituting the above expression (A) obtains $$\beta = \{V1+Q/(\alpha-1)+Q\}/\{V1+Q/(\alpha-1)\}.$$

Accordingly, V1 is expressed as:

$$V1 = Q/(\alpha-1) \times (\alpha-\beta)/(\beta-1). \quad (B)$$

From the above expressions (A) and (B), V3/V1 is expressed as:

$$V3/V1 = (\beta-1)/(\alpha-\beta). \quad (C)$$

Accordingly, from the above expression (C), V2/V1 is expressed as:

$$V2/V1 = (V3+V1)/V1 = V3/V1 + 1 = (\beta-1)/(\alpha-\beta)+1.$$

Thus, the above expression (2) is obtained.

The volume Q of air supplied by the pump 4 changes depending on pressure, and strictly speaking, the value of Q differs between the above (i) and (ii). However, the difference is slight against the difference between P10 and P20, and the value of Q in (i) and the value of Q in (ii) can be approximated to each other and regarded as the same value.

The predetermined time T is preferably a short time, for example, no less than 10 milliseconds and no more than 100 milliseconds. The larger the value of T, the larger the increase in pressure. Consequently, the value of Q in the above (i) and (ii) cannot be ignorable. In view that the pump 4 can be operated and stopped with high precision particularly for such a short time, a piezoelectric pump is preferably used as the pump 4.

The above method, however, is not a limitation. The volumes V1 and V2 can be directly measured to calculate V2/V1 in advance. In this case, however, measurement for various cuffs takes time and effort. In contrast, in the case where V2/V1 is calculated by the above method, the occurrence of air leak can be accurately detected in a simple manner without taking time and effort.

In the case where the cuff pressure is lower than the predetermined pressure, the control unit 3 may also detect an air-leak state (air leak from the cuff 2) in which the first space in the separation state is not kept airtight, and notify the air-leak state. Specifically, the sound generation unit 34 may provide a warning (notification) or the display unit 33 may display a warning massage, for example, when the air-leak state (air leak from the cuff 2) arises. Thus, a user such as a health care provider can recognize the air-leak state with more certainty.

There is a possibility that the measured cuff pressure is lower than the actual cuff pressure due to a measurement error of the pressure sensor 5. Accordingly, the air-leak state may be detected only when a decrease in the cuff pressure from the predetermined pressure exceeds a predetermined error range. In this case, misdetection of air leak can be reduced, and a load of a user, such as checking whether air leak occurs every misdetection, can be inhibited from increasing. For example, the error range is ±4 cmH$_2$O.

According to the present embodiment, the control unit 3 has not only a function of controlling the cuff pressure but also a function of correcting the value measured with the pressure sensor 5 to the cuff pressure (function of correcting a pressure decrease due to the volumes of the inner pipe 20, the connection tube 21, and another component of the cuff-pressure control device 1), as described above. Thus, the cuff pressure when the cuff 2 that is expanded in advance is in the separation state can be accurately measured.

In the case where the fact that air leak from the cuff 2 does not occur is confirmed, the pump 4 is operated to supply a gas (air) to the inside of the cuff 2 via the inner pipe 20, the connection tube 21, and the inflation passage, and the cuff pressure is increased to the appropriate predetermined pressure.

According to the present embodiment, the cuff pressure can be accurately measured, and air leak from the cuff 2 can be accurately detected. Thus, a user of the cuff-pressure control device 1, such as a health care provider, can readily know whether air leak from the cuff 2 occurs and appropriately deal with the case of the occurrence of air leak from the cuff 2. Consequently, secretions such as saliva or gastric juice can be prevented from flowing into the trachea due to air leak from the cuff 2, which decreases the cuff pressure and creates a space between the outer circumferential surface of the cuff 2 and the inner wall of trachea.

Second Embodiment

A cuff-pressure control device according to the present embodiment has a function of accurately measuring the actual cuff pressure while the cuff pressure is controlled so as to be the predetermined pressure, for example, during pressurization by the pump 4. That is, the cuff-pressure control device has a measure to correct an error due to pressure loss that occurs in the connection path (passage for a gas) from the pump 4 to the cuff 2 during pressurization. The present embodiment differs from the first embodiment in this point. The other typical structures and functions are the same as in the first embodiment, and a duplicated description is omitted.

Specifically, according to the present embodiment, the control unit 3 controls the cuff pressure through the following procedures (a) to (c).

(a) A gas is first supplied to the inside of the cuff 2 in the deflated state with the pump 4. At this time, the internal pressure of the inner pipe 20 is continuously measured with the pressure sensor 5. Subsequently, a first pressure that is the internal pressure of the inner pipe 20 that is measured with the pressure sensor 5 is acquired, and the operation of the pump 4 is suspended (at the same time) at a first juncture (see FIG. 6 and FIG. 7) after the supply of the gas to the inside of the cuff 2 is started and the internal pressure of the inner pipe 20 reaches equilibrium for the first time.

(b) A second pressure that is the internal pressure of the inner pipe 20 that is measured with the pressure sensor 5 is acquired at a second juncture (see FIG. 6 and FIG. 7) after the operation of the pump 4 is stopped and the internal pressure of the inner pipe 20 reaches equilibrium.

(c) The pump 4 is operated again after the second juncture. At this time, a correction value of the cuff pressure is calculated in a manner in which an absolute value of a difference between the first pressure and the second pressure (a pressure increase due to pressure loss) is subtracted from the internal pressure of the inner pipe 20 that is measured with the pressure sensor 5. The pump 4 is operated in accordance with the correction value (real cuff pressure) to control the cuff pressure.

Figure 6:
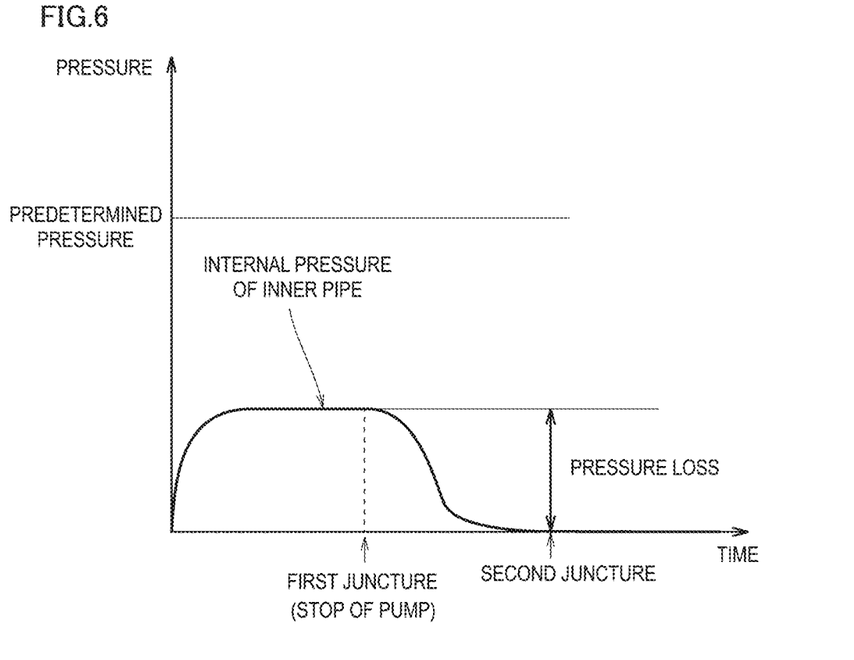
FIG. 6 schematically illustrates a graph of variation in pressure in an inner pipe of a cuff-pressure control device according to a second embodiment.
Figure 7:
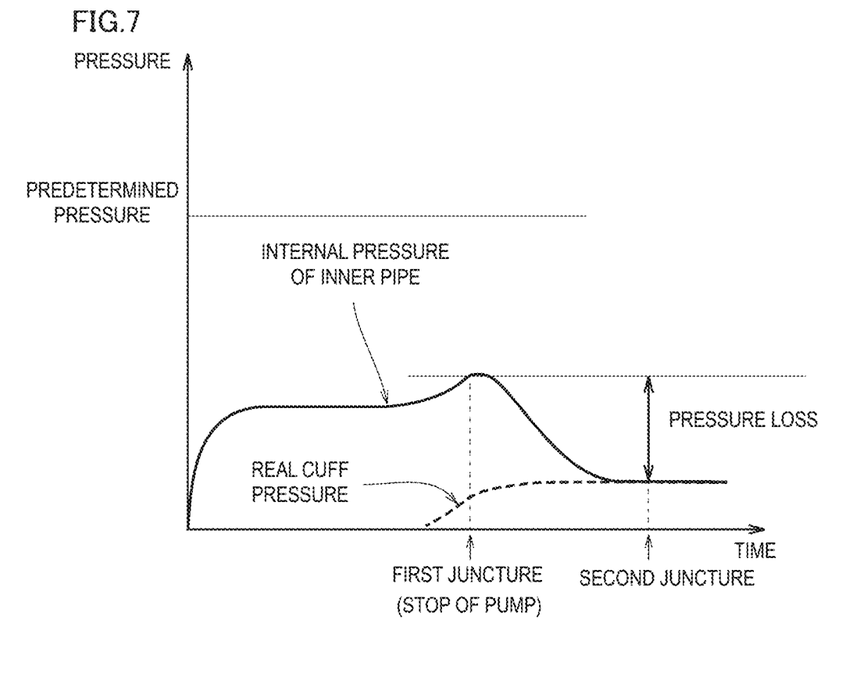
FIG. 7 schematically illustrates a graph of variation in the real cuff pressure and variation in pressure in an inner pipe of a cuff-pressure control device according to a modification to the second embodiment.

As illustrated in FIG. 6, the first juncture in the above (a) may be a juncture at which the internal pressure of the inner pipe 20 reaches equilibrium for the first time and in the equilibrium after the supply of the gas to the inside of the cuff 2 is started, or may be a juncture after the equilibrium as illustrated in FIG. 7.

In the former case (FIG. 6), the pump 4 is stopped in a state where the cuff 2 is not completely expanded. Accordingly, it is thought that the gas in the connection path delays due to pressure loss, and the cuff pressure does not increase even when the gas flows into the cuff 2, and, as illustrated in FIG. 6, the cuff pressure and the internal pressure of the inner pipe 20 are zero in the equilibrium after the pump 4 is stopped. For this reason, the first pressure is equal to the pressure loss that occurs in the connection path from the pump 4 to the cuff 2. Accordingly, the second pressure may not be acquired in the above (b), and the first pressure may be regarded as the pressure loss to make correction in the same manner as in the above (c).

In the latter case (FIG. 7), the pump 4 is stopped after the cuff 2 is completely expanded and the cuff pressure starts to increase. Accordingly, as illustrated in FIG. 7, it is thought that the cuff pressure and the internal pressure of the inner pipe 20 are larger than zero in the equilibrium after the pump 4 is stopped. In this case, it is necessary to acquire the second pressure in the above (b) in order to calculate the pressure loss. Thus, the procedures (a) to (c) enable the pressure loss to be calculated in both the former and latter cases.

Figure 5:
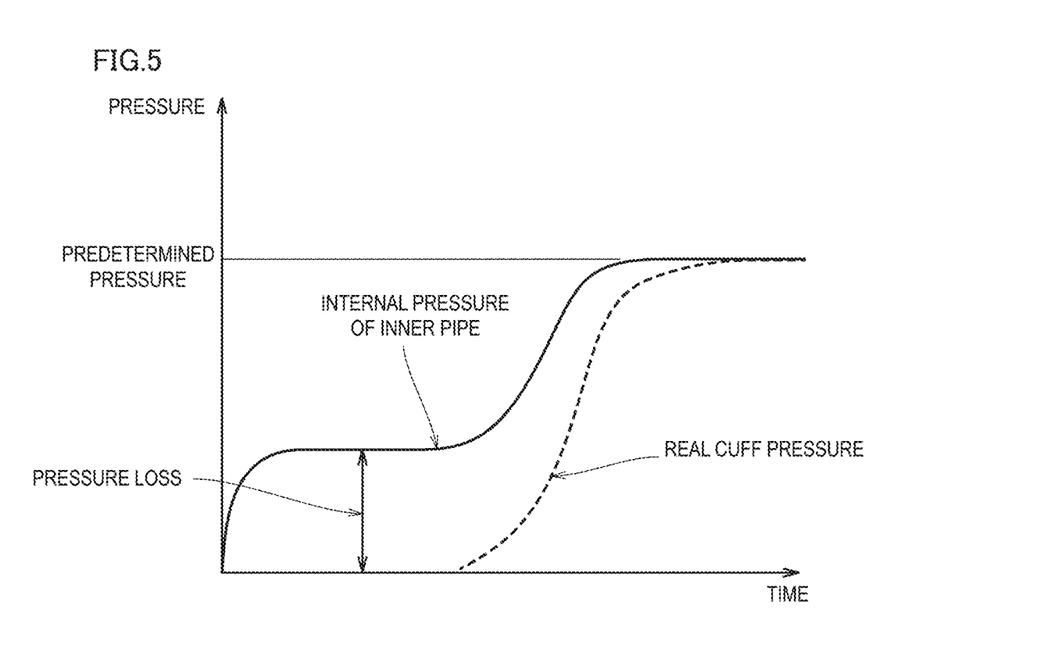
FIG. 5 schematically illustrates a graph of the relationship between the real cuff pressure and the pressure in the inner pipe of the cuff-pressure control device while the cuff is pressurized.

As illustrated in FIG. 5, the higher the cuff pressure, the smaller the amount of the gas supplied from the pump 4, and the smaller the pressure loss. Accordingly, to calculate the pressure loss more precisely, it is desirable that the relationship between the pressure loss and the amount of the gas be investigated in advance, and in the above (c), the "absolute value of the difference between the first pressure and the second pressure" is corrected in accordance with the amount of the gas at the time.

FIG. 5 schematically illustrates a graph of the relationship between the real cuff pressure (dashed line) and the internal pressure (solid line) of the inner pipe 20 that is measured with the pressure sensor 5 while the cuff 2 is pressurized. As illustrated in FIG. 5, in the case where the pump 4 is connected to the cuff 2 with the connection tube 21 and the inflation passage, which is a relatively narrow passage, interposed therebetween, the operation of the pump 4 makes the internal pressure of the inner pipe 20 that is measured with the pressure sensor 5 higher than the actual cuff pressure due to the pressure loss (for example, no less than 3 $cmH_2O$ and no more than 20 $cmH_2O$) caused by, for example, the inflation passage even during a short time (for example, 1 to 30 seconds) until the cuff pressure reaches the predetermined pressure.

For this reason, an existing method in which the internal pressure of the inner pipe 20 is merely measured carries a risk that the pump 4 is stopped before the actual cuff pressure increases to the predetermined pressure, and that the cuff pressure cannot increase to the predetermined pressure. In particular, in the case of the spot use, there is a risk that a user thinks the actual pressure reaches the predetermined pressure and detaches the cuff-pressure control device even when the actual cuff pressure does not reach the predetermined pressure.

While the cuff pressure is decreased with the exhaust valve 6, the internal pressure of the inner pipe 20 is lower than the actual cuff pressure due to the pressure loss of the inflation passage connected to the cuff 2, although this is not illustrated. For this reason, in the case where the internal pressure of the inner pipe 20 is merely measured, there is a risk that the exhaust valve 6 is closed before the actual cuff pressure decreases to the predetermined pressure, and that the cuff pressure cannot decrease to the predetermined pressure.

In contrast, according to the present embodiment, the cuff pressure can be controlled on the basis of the value obtained by correcting the internal pressure of the inner pipe 20 that is measured with the pressure sensor 5 to the actual cuff pressure. Thus, the cuff pressure can be controlled so as to be the appropriate predetermined pressure more accurately than in the existing method in a manner in which the accurate cuff pressure is monitored even during a short time until the cuff pressure is adjusted to the predetermined pressure. Consequently, secretions such as saliva can be prevented from reaching the lungs due to a cuff pressure lower than the appropriate value. In addition, the tracheal wall can be prevented from being excessively pressed due to a cuff pressure higher than the appropriate value.

According to the present embodiment, in view that the pump 4 can be operated and stopped with high precision particularly for such a short time during which the cuff pressure is adjusted to the predetermined pressure, a piezoelectric pump is preferably used as the pump 4.

It should be understood that the embodiments are described by way of example in all their aspects, not by way of limitation. The scope of the present disclosure is not shown by the embodiments but by the scope of claims. The scope of the present disclosure includes all modifications having the same content and range as the scope of claims.

1 cuff-pressure control device
2 cuff
3 control unit
4 pump
5 pressure sensor
6 exhaust valve
8 tracheal tube
8a main passage
10 housing
20 inner pipe
21 connection tube
22a passage
22b inflation tube
22c, 22d opening
23a, 23b luer connector
30a, 30b power supply
31 memory unit
32 input unit
33 display unit
34 sound generation unit
41 check valve
91 trachea
91a inner wall
92 esophagus
93 epiglottis
94 oral cavity.

The invention claimed is:

1. A cuff-pressure control device used to appropriately maintain a cuff pressure that is a pressure of an inside of a cuff, comprising:
a pump configured to supply a gas to the inside of the cuff;
an inner pipe connected to the pump;
a pressure sensor configured to measure a pressure of an inside of the inner pipe; and
a control unit configured to cause the pump to operate and thereby controlling the cuff pressure,
wherein the cuff is separable from the cuff-pressure control device, and, in a separation state in which the cuff is separated from the cuff-pressure control device, a first space in communication with the cuff is kept airtight such that the cuff pressure is maintained at a predetermined pressure, and
wherein the control unit is configured to adjust a pressure in the cuff-pressure control device to a pressure of the first space before the cuff is connected to the cuff-pressure control device in a connection state in which the cuff in the separation state is connected to the cuff-pressure control device and the cuff and the inner pipe are in communication with each other.

2. The cuff-pressure control device according to claim 1, wherein the control unit is further configured to cause the pressure sensor to measure a pressure P2 of a second space in communication with the cuff and the inner pipe without operating the pump, and
wherein the control unit is further configured to calculate the cuff pressure that is equal to a pressure P1 of the first space in the separation state right before the connection state by using the pressure P2 of the second space and the following expression (1):

$$P1 = P2 \cdot V2/V1, \quad (1)$$

where V1 is a volume of the first space, and V2 is a volume of the second space.

3. The cuff-pressure control device according to claim 2, wherein the control unit is further configured to:
(i) cause the pump to operate for a predetermined time to pressurize a third space in communication with the inner pipe in the separation state, cause the pressure sensor to measure a pressure P30 of the third space before pressurization and a pressure P31 of the third space after the pressurization, and calculate a ratio α of P31 to P30,
(ii) cause the pump to operate for the predetermined time to pressurize the second space in the connection state and in a state where the cuff expands and an increase in a volume of the cuff when the first space is pressurized is ignorable, cause the pressure sensor to measure a pressure P20 of the second space before pressurization and a pressure P21 of the second space after the pressurization, and calculate a ratio β of P21 to P20, and
(iii) calculate V2/V1 by using α, β, and the following expression (2):

$$V2/V1 = (\beta - 1)/(\alpha - \beta) + 1 \quad (2).$$

4. The cuff-pressure control device according to claim 1, wherein the control unit is further configured to detect an air-leak state in which the first space is not kept airtight in the separation state, and to notify of the air-leak state in a case where the pressure P1 of the first space is lower than the predetermined pressure.

5. The cuff-pressure control device according to claim 1, wherein the pump is a piezoelectric pump.

6. A cuff-attached tracheal tube, comprising:
the cuff-pressure control device according to claim 1;
a tracheal tube having a main passage through which a gas is supplied to an inside of a trachea; and
the cuff.

7. A ventilator comprising the cuff-attached tracheal tube according to claim 6.

8. The cuff-pressure control device according to claim 2, wherein the control unit is further configured to:
(i) cause the pump to operate for a predetermined time to pressurize a third space in communication with the inner pipe in the separation state, cause the pressure sensor to measure a pressure P30 of the third space before pressurization and a pressure P31 of the third space after the pressurization, and calculate a ratio α of P31 to P30,
(ii) cause the pump to operate for the predetermined time to pressurize the second space in the connection state and in a state where the cuff expands and an increase in a volume of the cuff when the first space is pressurized is ignorable, cause the pressure sensor to measure a pressure P20 of the second space before pressurization and a pressure P21 of the second space after the pressurization, and calculate a ratio α of P21 to P20, and
(iii) calculate V2/V1 by using α, β, and the following expression (2):

$$V2/V1 = (\beta - 1)/(\alpha - \beta) + 1 \quad (2).$$

9. The cuff-pressure control device according to claim 2, wherein the control unit is further configured to detect an air-leak state in which the first space is not kept airtight in the separation state, and to notify of the air-leak state in a case where the pressure P1 of the first space is lower than the predetermined pressure.

10. The cuff-pressure control device according to claim 3, wherein the control unit is further configured to detect an air-leak state in which the first space is not kept airtight in the separation state, and to notify of the air-leak state in a case where the pressure P1 of the first space is lower than the predetermined pressure.

11. The cuff-pressure control device according to claim 2, wherein the pump is a piezoelectric pump.

12. The cuff-pressure control device according to claim 3, wherein the pump is a piezoelectric pump.

13. The cuff-pressure control device according to claim 4, wherein the pump is a piezoelectric pump.

14. A cuff-attached tracheal tube, comprising:
the cuff-pressure control device according to claim 2;
a tracheal tube having a main passage through which a gas is supplied to an inside of a trachea; and
the cuff.

15. A cuff-attached tracheal tube, comprising:
the cuff-pressure control device according to claim 3;
a tracheal tube having a main passage through which a gas is supplied to an inside of a trachea; and
the cuff.

16. A cuff-attached tracheal tube, comprising:
the cuff-pressure control device according to claim 4;
a tracheal tube having a main passage through which a gas is supplied to an inside of a trachea; and
the cuff.

17. A cuff-attached tracheal tube, comprising:
the cuff-pressure control device according to claim 5;
a tracheal tube having a main passage through which a gas is supplied to an inside of a trachea; and
the cuff.

* * * * *